United States Patent [19]

Gallo-Torres et al.

[11] 4,107,188

[45] Aug. 15, 1978

[54] PREGNANES

[75] Inventors: Hugo Gallo-Torres, Livingston; James Guthrie Hamilton, Nutley; Perry Rosen, North Caldwell; Ann Clare Sullivan, Cedar Grove, all of N.J.

[73] Assignee: Hoffmann-La Roche Inc., Nutley, N.J.

[21] Appl. No.: 790,165

[22] Filed: Apr. 22, 1977

[51] Int. Cl.² ............................................... C07J 9/00
[52] U.S. Cl. .................................. 260/397.1; 424/238
[58] Field of Search ..................................... 260/397.1

[56] References Cited

U.S. PATENT DOCUMENTS

| | | | |
|---|---|---|---|
| 3,801,607 | 4/1974 | Goffinet | 260/397.1 |
| 3,836,550 | 9/1974 | Jones | 260/397.1 |

*Primary Examiner*—Elbert L. Roberts
*Attorney, Agent, or Firm*—Samuel L. Welt; Bernard S. Leon; William H. Epstein

[57] ABSTRACT

The compound 5(3,12-dihydroxy-pregnan-20-yl)-pentanoic acid and 7-(3,12-dihydroxy-pregnan-20-yl)-heptanoic acid as well as ester and unsaturated derivatives thereof useful for decreasing the level of lipids such as cholesterol and triglycerides.

9 Claims, No Drawings

PREGNANES

SUMMARY OF INVENTION

In accordance with this invention, compounds of the formula:

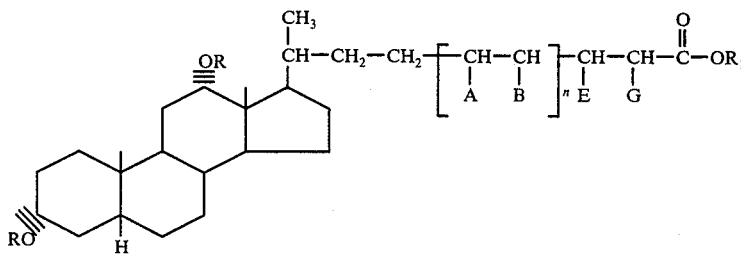

wherein R is hydrogen or lower alkanoyl; $R_1$ is lower alkyl or hydrogen, A and B are individually hydrogen or taken together form a carbon to carbon bond; E and G are individually hydrogen or taken together form a carbon to carbon bond; $n$ is an integer from 0 to 1 with the proviso that when $n$ is 1, and A and B are hydrogen; E and G are also hydrogen and pharmaceutically acceptable salts thereof have been found to be active for decreasing lipid levels such as triglyceride or cholesterol levels.

All of the compounds of formula I are active as triglyceride lowering agents. Of the compounds of formula I, all of the compounds except those compounds where when $n$ is $o$, E and G form a double bond are active as cholesterol lowering agents, i.e. compounds of the formula:

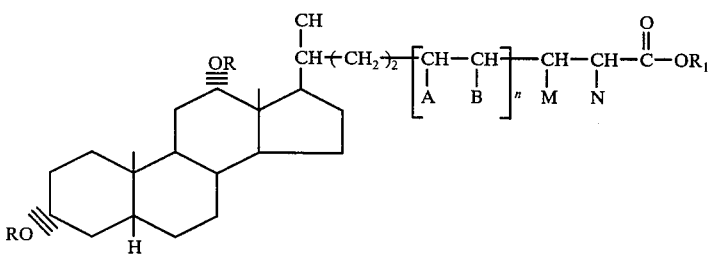

wherein R, $R_1$ and $n$ are as above, A and B are hydrogen or taken together form a carbon to carbon bond, M and N are hydrogen or taken together form a carbon to carbon bond; with the proviso that when $n$ is 1 and A and B are hydrogen, M and N are hydrogen; and with the further proviso that when $n$ is $o$, M and N are hydrogen; and pharmaceutically acceptable salts thereof are active as cholesterol lowering agents.

The compounds of formula I are produced from compounds of the formula

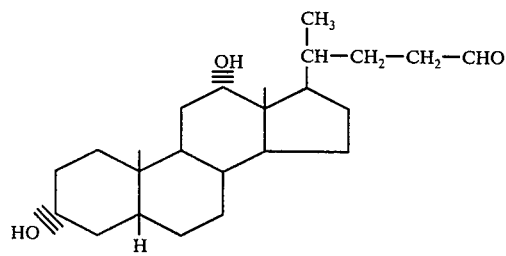

SUMMARY OF INVENTION

As used throughout this application, the term "lower alkyl" includes both straight and branched chain alkyl groups containing from 1 to 7 carbon atoms, such as methyl, ethyl, propyl and isopropyl. As used throughout this application, the term "lower alkoxy" includes lower alkoxy groups containing from 1 to 7 carbon atoms such as methoxy, ethoxy, isopropoxy, etc. The term "lower alkanoyl" includes lower alkanoyl groups containing from 1 to 7 carbon atoms such as formyl, acetyl, propionyl, etc.

The term "alkali metal" as used herein designates all of the alkali metals such as lithium, sodium, potassium, etc. with sodium being preferred. The term "halogen" includes all four halogens such as chlorine, bromine, iodine and fluorine, with bromine or chlorine being preferred.

The term "aryl" as used herein signifies mononuclear aromatic hydrocarbons such as phenyl tolyl, etc. as well as polynuclear aryl groups such as napthyl, anthryl phenanthryl, azulyl, etc.

The compounds of formula I where R is hydrogen, $n$ is $o$, i.e. compounds of the formula

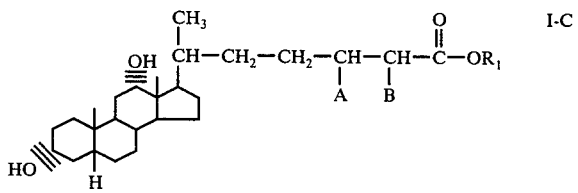

where $R_1$, A and B are as above are prepared from the compound of formula II. In the first step, the compound of formula II is esterified with a lower alkanoic acid to produce a compound of the formula:

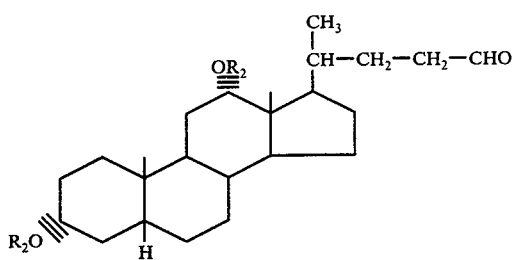

III wherein $R_2$ is lower alkanoyl. This reaction is carried out by esterifying the compound of formula II by reaction with a lower alkanoic acid or a reactive derivative thereof. Any conventional method of esterification can be utilized to produce the compound of formula III. Among the preferred lower alkanoyl groups are formyl and acetyl.

The compound of formula III is converted to a compound of the formula:

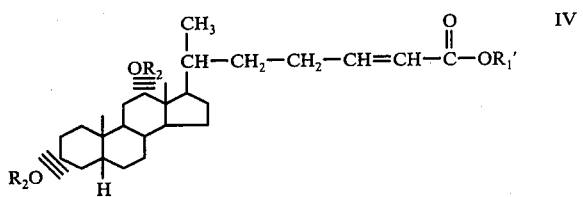

IV where $R_2$ is lower alkanoyl and $R_1'$ is lower alkyl by reaction with a compound of the formula

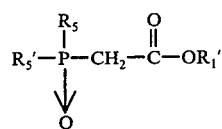

V wherein $R_5$ and $R_5'$ are aryl, aryloxy, or lower alkoxy and $R_1'$ is as above or a compound of the formula:

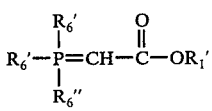

VI wherein $R_6$, $R_6'$ and $R_6''$ are aryl or di(lower alkyl)-amino.

The reaction of the compound of formula III with a compound of formula V is carried out by a Horner reaction. Any of the conditions conventional in carrying out a Horner reaction can be utilized. The reaction of the compound of formula III with a compound of formula VI is carried out via a Wittig reaction. Any of the conditions conventional in Wittig reactions can be utilized in carrying out this reaction.

The compound of formula IV can be hydrogenated to produce a compound of the formula:

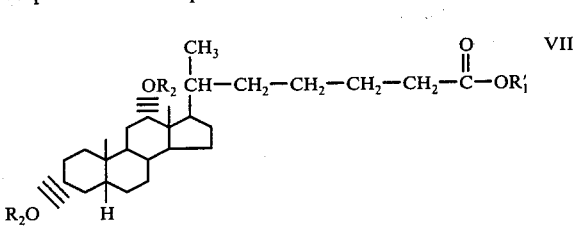

VII wherein $R_2$ and $R_1'$ are as above; Any conventional method of catalytic hydrogenation can be used to affect the conversion.

The compound of formula VII is converted to the compound of Formula I-C where A and B are hydrogen and $R_1$ is hydrogen by ester hydrolysis. Any conventional method of ester hydrolysis can be utilized to affect this conversion. If it is desired to produce a compound of formula I-C where A and B are hydrogen and $R_1'$ is lower alkyl, the compound of formula I-C where A, B and $R_1$ are hydrogen is esterified with a lower alkanol or a reactive derivative thereof. Any conventional method of esterifying an organic acid with a lower alkanol can be utilized to convert the compound of formula I-C where A, B and $R_1$ are hydrogen to the corresponding compound of formula I-C where $R_1$ is lower alkyl.

On the other hand, the compound of formula IV can be converted directly to a compound of the formula

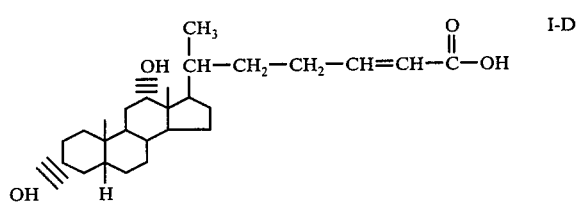

I-D by ester hydrolysis as described hereinbefore. The compound of formula I-D can, if desired, be converted to the compound of formula I-C where A and B form a double bond and $R_1$ is lower alkyl by esterification with a lower alkanol. Any conventional method of esterification can be utilized to carry out this conversion. The compound of formula I where $n$ is 1, i.e. a compound of the formula:

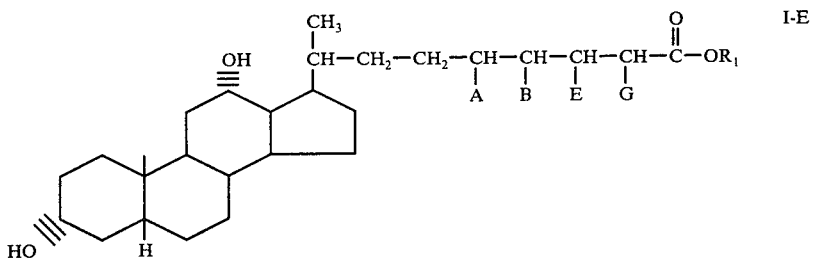

I-E wherein $R_1$ is as above; A, B, E and G are as above, with the proviso that when A and B are hydrogen, E and G are also hydrogen and are also produced from a compound of formula III. In the first step of this synthesis a compound of formula III is reacted with a compound of the formula:

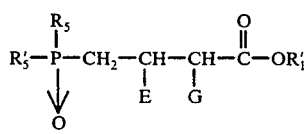

wherein $R_5$, $R_5'$, $R_1'$, E and G are as above; or a compound of the formula:

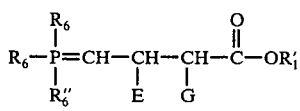

wherein $R_6$, $R_6'$, $R_6''$, $R_1'$ and E and G are as above to produce a compound of the formula

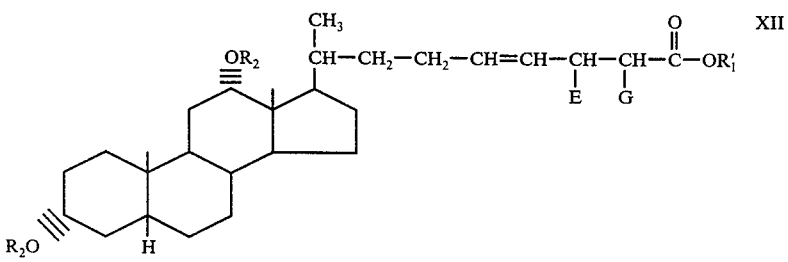

wherein $R_2$, $R_1'$, E and G are as above.

The reaction of the compound of formula III with a compound of the formula X is carried out in the same manner as described in connection with the reaction of a compound of the formula III with a compound of the formula V. The reaction of the compound of the formula III with a compound of the formula XI is carried out in the same manner as described in connection with the reaction of a compound of formula III with a compound of the formula VI.

The compound of formula XII can be converted to the compound of the formula

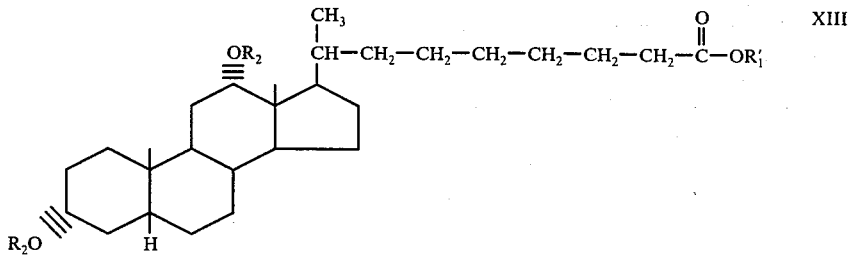

where $R_1'$ and $R_2$ are as above. This reaction is carried out by catalytic hydrogenation in the same manner as described in connection with the conversion of a compound of formula IV to a compound of formula VII.

The compound of formula XIII can be converted to a compound of formula

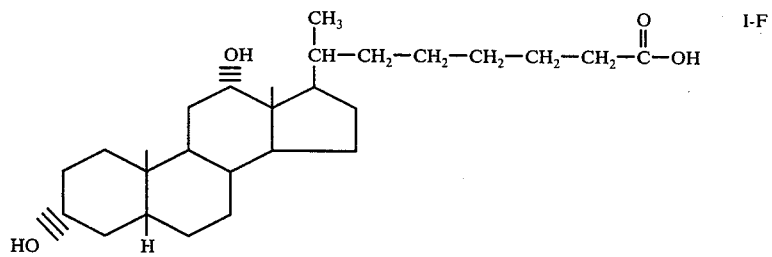

by ester hydrolysis utilizing conventional hydrolysis techniques. On the other hand, the compound of formula XII can be hydrolyzed in the same manner to produce a compound of the formula:

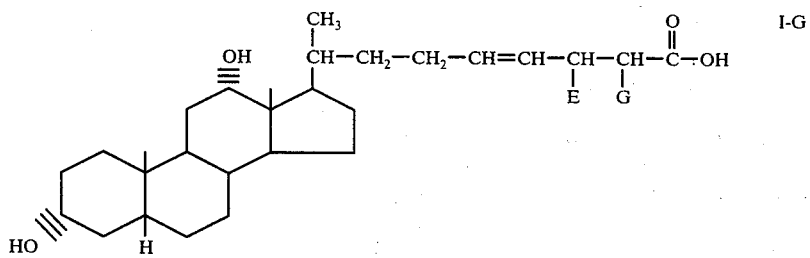

wherein E and G are as above.

Both the compound of formula I-G and I-F can be esterified in the conventional manner with a lower alkanol to produce the compound of formula I-E where $R_1$ is lower alkyl. Any conventional method of esterifying an organic acid with a lower alkanol can be utilized to carry out this procedure.

The 3 and 12 dihydroxy groups on the compounds of formula I-C where $R_1$ is hydrogen I-D, I-F and I-G can be esterified to produce a compound of formula I where $R_1$ is hydrogen and R is lower alkanoyl by esterification with a lower alkanoic acid or a reactive derivative thereof in the same manner as described in connection with the esterification of a compound of formula II to produce a compound of formula III.

In accordance with aother embodiment of this invention, the compound of formula III can be prepared from a compound of the formula

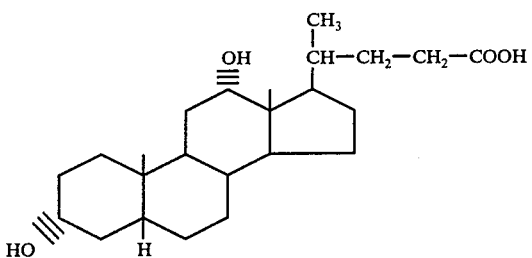

via the following intermediates

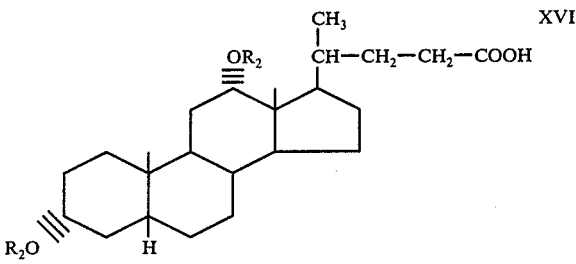

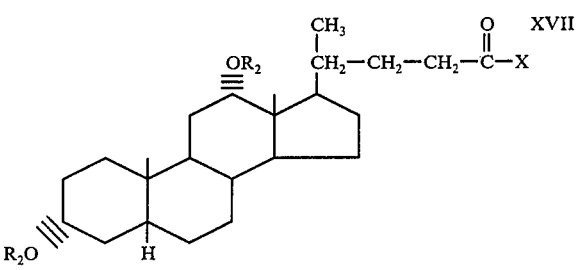

wherein $R_2$ is as above; and X is halogen.

The compound of formula XV is converted to the compound of formula XVI by esterification with a lower alkanoic acid or a reactive derivative thereof in the manner described in connection with the esterification of a compound of II to a compound of formula III. The compound of formula XVI is converted to the compound of formula XVII by treatment with a halogenating agent. Any conventional method of converting an organic acid to an acid chloride can be utilized in carrying out this reaction. Among the preferred methods is by treating the compound of formula XVI with a halogenating agent such as oxalyl chloride. The compound of formula XVII is converted into the compound of formula III utilizing any method conventional for reducing an acid halide to an aldehyde. Among the preferred methods is Rosenmund reduction.

Administration of compounds of formula I-A result in the inhibition of activity in hypercholesteremic mammals of the rate limiting enzyme which controls the rate of cholesterol synthesis in mammals, and thus results in a lowering of the cholesterol levels of the hypercholesteremic mammal being treated. In fact, the inhibition of cholesterol synthesis results in a decrease of the natural distribution of cholesterol into the plasma of the mammal being treated, and consequently will lead to a reversal of the process whereby excessive cholesterol has been previously deposited which results in the formation of artherosclerotic plaque. Thus, administration of the compounds of Formula I-A in the practice of this invention to hypercholesteremic mammals will apparently lead to a depletion of excessive cholesterol deposits in the body of said mammal, for example, artherosclerotic plaque.

The lowering of the cholesterol levels in mammals by the administration of the compound of formula I-B can be seen from the fact that when 100 mg of 7-(3alpha, 12alpha-dihydroxy-5beta-pregnane-20-yl)-3,5-heptadienoic acid was administered orally to female albino rats, the cholesterol level in the lymph was decreased after administration by 60% over the first 8 hours and 91% over the next 9 to 24 hr. period after administration as compared to the control. In this procedure, female albino rats (Charles River), weighing 300 ± 10 g were kept on a Purina chow diet ad libitum until the time of operation. In addition to thoracic duct cannula, the animals had a double catheterization of the upper part of the common bile duct. This preparation enabled the production of lymph at a constant rate, the infusion of a bile salt, and the simultaneous collection of bile. All animals received, after operation, a continuous duodenal infusion of sodium taurocholate (Na-TC) in 0.85% NaCl. One day after operation, the rats were given, by stomach intubation, an emulsion containing about 4% triolein, 20 $\mu$C of 4-$^{14}$C-cholesterol (Specific Activity 61.7 mC/mM, 159 $\mu$ C/mg), 2 mg of cholesterol, in addition to protein, carbohydrate, and saline. Both the Na-TC and the cholesterol carrier employed gave a single spot on either thin layer or glass fiber chromatograph so no further purification was attempted. The commercial glyceryl trioleate contained a large percentage of di- and monoolein. Tiolein was, therefore, purified by passage through a silicic acid column; the final product gave a single spot on either glass fiber paper or thin layer chromatography. The radiocholesterol employed was found to be > 97% pure. To 4 ml of this emulsion was added 100 mg of either Na-TC (control group) or the compound of formula I-A. This mixture was given orally to the animals. The sampling of thoracic duct lymph was divided into two collecting periods, 0–8 and 9–24 $h$ after emulsion administration. Lymph specimens were lyophilized and the lipids in the residue were extracted with ethanolisopropyl ether, 2:1 parts by volume, by procedure described in Gallo-Torres, et al; Bio phys. Acta, 176 605–615 (1969). An aliquot of the lipid extract was placed on a small piece of glass fiber paper and counted. Another aliquot was used for the separation of cholesterol and its esters by glass fiber paper chromatography.

The effect of the test compound on the appearance of total $^{14}$C-cholesterol in the thoracic duct lymph of rats was given above. Of the dose administered to the control animals, 5 × 15$^5$ dpm were recovered in the first 8 h and 3.4 × 10⁶ dpm inthe period of 9-24 h following administration of the emulsion. The tolerance of cholesterol as given above in the % decrease in the 4-$^{14}$C-cholesterol over the control appearing in the lymph during the specified period.

The compound of Formula I decreases the level of lipids such as triglyceride in biological systems. The compounds of Formula I decrease the triglyceride levels in systems in which they are administered. Therefore, the compounds of formula I may be administered to hypertriglyceridemic mammals to inhibit the pancreatic lipase, the enzyme which controls the hydrolysis of triglycerides in biological systems such as mammals. Therefore, the administration of the compound of Formula I to biological systems results in a lowering of the triglyceride absorbed by the gastro-intestinal tract. Therefore, the compounds of this invention by the inhibition of the pancreatic lipase significantly reduce the fat caloric absorption in mammals and significantly aid in the treatment of obesity.

Dietary long-chain triglycerides must be hydrolyzed by pancreatic lipase in the duodenum before absorption can occur. Compounds of formula I which inhibit pancreatic lipase would significantly reduce fat caloric absorption and represent useful antiobesity and hypotriglyceridemic agents. The capacity of compounds of formula I to inhibit rat pancreatic lipase in vitro is seen by the action of the following compounds:

Compound A = 7(3α,12α-dihydroxy-5β-pregnane-20-yl)-3,5-heptadienoic acid

Compound B = 5-(3α,12α-dihydroxy-5βpregnane-20-yl)pentanoic acid

The ability of compounds to inhibit rat pancreatic lipase is determined by analyzing the nmoles of free fatty acid [oleic acid] released from [$^{14}$C]-triolein. Compounds of A and B are added to an emulsion consisting of: 200,000 dmp $^{14}$C-triolein, 7.5 mg triolein, 0.75 mg sodium taurocholate, 15 mg bovine serum albumin and 0.9 ml 0.2 M tris-HCl - 0.15 M NaCl, pH 8.6, per assay. Water and/or pancreatic lipase is added to make an assay volume of 1.0 ml. The emulsion is incubated for 20 min. at 37° C in a shaking water bath. The reaction is stopped by the addition of isopropanol; H$_2$SO$_4$(40:1). The lipids are extracted twice with 3 ml volumes of hexane. The liberated fatty acids are extracted with 2 ml of 0.1 N aqueous KOH in 50% methanol. A 1 ml aliquot of the KOH layer is paced in a scintillation vial with 10 ml of 2,5-bis-2-(5-tertiary butyl benzoxazolyl)thiophene. The radioactivity is determined by a scintillation counter. Data are expressed as nmoles free fatty acid [oleic acid] releated.

TABLE

| INHIBITION OF RAT PANCREATIC LIPASE ACTIVITY | |
|---|---|
| Test Compound | Pancreatic Lipase Activity Ki (mM) |
| Compound A | 1 |
| Compound B | 9 |

The compound of Formula I may be utilized in the form of a pharmaceutically acceptable non-toxic basic salts. Preferred salts for this purpose include the alkali metals, e.g., sodium or potassium; the alkaline earth metals, e.g. calcium or complex salts such as ammonium or substituted ammonium salts such as ammonia, di- or tri-alkyl ammonium salt or a mono, di- or tri-hydroxyalkyl ammonium salt. The compounds of Formula I can be utilized in the form of conventional pharmaceutical preparations; for example, the aforesaid compounds can be mixed with conventional inorganic inert pharmaceutical carriers suitable for parenteral or enteral administration such as, for example, water, gelatin, lactose, starch, magnesium stearate, talc, vegetable oil, gums or the like. They can be administered in conventional pharmaceutical forms, e.g., solid forms, for example, tablets, dragees, capsules, suppositories or the like; or in liquid forms, for example, suspensions of emulsions. Moreover, the pharmaceutical compositions containing compounds of this invention can be subjected to conventional pharmaceutical expedients such as sterilization, and can contain conventional pharmaceutical excipients such as preservatives.

A suitable pharmaceutical dosage unit can contain from about 16 to 600 mg. of the compound of Formula I or its salts. Suitable parental dosage regimens in mammals comprise from 1 mg/kg to about 100 mg/kg per day. However, for any particular subject, the specific dosage regimen should be adjusted according to the individual needs and the professional judgment of the person administering or supervising the administration of the aforesaid compounds. It is to be understood that the dosages set forth herein are exemplary only and that they do not, to any extent, limit the scope or practice of this invention.

EXAMPLE 1

5-(3α,12α-Diformyloxy-5β-pregnane-20-yl)-trans-2-pentenoic acid methyl ester

A solution of 64.8 g of (0.149) of 3α,12α-dihydroxy-24-cholanal, diformate and 55 g (10% excess) of carbomethoxymethylene triphenylphosphorane $^{12}$in 250 ml of dry benzene was refluxed for 6 hr. The solvent was then removed under reduced pressure and the residue treated with 400 ml of a 3:1 solution of hexane-ether. The resulting precipitate was filtered to give 39 g of crude triphenylphosphine oxide. The filtrate was concentrated, dissolved in a minimum of benzene and washed through 600 g of silica gel with a 2% ethyl acetate-benzene solution. The solvent was removed and the residue crystallized from hexane to give 49 g of 5-(3α,12α-diformyloxy-5β-pregnane-20-yl)-trans-2-pentenoic acid methyl ester mp 112°-115°.

Anal. Calcd for C$_{29}$H$_{44}$O$_6$: C, 71.28; H, 908. Found: C, 71.45; H, 9.17.

EXAMPLE 2

5-(3α,12α-Dihydroxy-5β-pregnane-20-yl)-trans-2-pentenoic acid

A mixture of 5.2 g of 5-(3α,12α-diformyloxy-5β-pregnane-20-yl)-trans-2-pentenoic acid methyl ester and 30 ml of 5 N aqueous sodium hydroxide was added and the mixture heated to reflux. The solution was then cooled, treated with charcoal and filtered with suction through a bed of diatomaceous earth. The filtrate was then cooled to 0° and with stirring was acidified to a pH3 by the dropwise addition of concentrated hydrochloric acid. The resulting precipitate was filtered and air dried overnight under house vacuum. Crystallization from methyl ethyl ketone gave 3 g of 5-(3α,12α-dihydroxy-5β-pregnane-20-yl)-trans-2-pentenoic acid, mp 204°-208°.

Anal. Calcd for C$_{26}$H$_{42}$O$_4$: C, 74.60; H, 10.11. Found: C, 74.47; H, 10.04.

EXAMPLE 3

5-(3α,12α-Diformyloxy-5β-pregnane-20-yl)pentanoic acid methyl ester

A mixture of 1 g of 10% Pd/C and 7.6 g of 5-(3α,12α-diformyloxy-5β-pregnane-20-yl)-trans-2-pentenoic acid methyl ester in 100 ml of ethyl acetate was hydrogenated at atmospheric pressure. After completion of the reaction, the catalyst was filtered and the solvent removed under reduced pressure. Trituration of the residue with ether-hexane afforded 7.5 g of 5-(3α,12α-diformyloxy-5β-pregnane-20-yl)-pentanoic acid methyl ester mp 67-72°.

Anal. Calcd for $C_{29}H_{46}O_6$: C, 70.98; h, 9.45. Found: C, 70.77; H, 9.58.

EXAMPLE 4

5-(3α,12α-Dihydroxy-5β-pregnane-20-yl)pentanoic acid

A solution of 7.2 g of 5-(3α,12α-diformyloxy-5β-pregnane-20-yl)pentanoic acid methyl ester, 50 ml of methanol, 50 ml of 2N methanolic sodium hydroxide solution and 10 ml of water was refluxed for 2 hr. At the end of this time, the methanol was removed under reduced pressure and 300 ml of water was added to the residue. The solution was treated with charcoal and filtered through a bed of diatomaceous earth. The solution was then cooled to 0° and with stirring acidified (pH3) by the dropwise addition of concentrated aqueous hydrochloric acid. The precipitate was filtered and dried overnight under house vacuum. Crystallization from methyl ethyl ketone gave 4 g of 5-(3α,12α-dihydroxy-5β-pregnane-20-yl)pentanoic acid, mp 191°-193°.

Anal. Calcd for $C_{26}H_{44}O_4$: C, 72.24; H, 10.54. Found: C, 73.90; H, 10.32.

EXAMPLE 5

3α,12α-Diacetoxycholan-24-al

To a solution of 38 g of deoxycholic acid in 400 ml of acetic acid and 120 ml of acetic anhydride was added dropwise 38 ml of 70% perchloric acid, the temperature not being allowed to rise above 38°. After the addition, the reaction mixture was stirred for 0.5 hr and was then poured with stirring into 4 liters of ice water. The resulting diacetoxy compound was filtered and air dried overnight under house vacuum. The dried diacetoxy derivative was then added to 50 ml of oxalyl chloride and the resulting solution stirred overnight. Heptane was then added and the solvent and excess oxalyl chloride was removed at reduced pressure. Traces of oxalyl chloride were removed by adding fresh heptane and removing it under reduced pressure as before. The residue soon set to a crystalline mass (trituration with hexane of a small amount of the acid chloride gave colorless crystals, mp 130°).

The crude acid chloride was dissolved in 1 liter of dry benzene to which was added 4 g of 10% Pd/C. The reaction mixture was placed under a vacuum (water aspirator) of about 30 mm such that the benzene began to reflux at a temperature of approximately 30°-32°. Hydrogen was then introduced into the mixture. The exiting gases were passed through 300 ml of ice cold water and the reaction followed by titration of the hydrogen chloride being evolved. At the end of 3.5 hr the theoretical amount of hydrogen chloride had been eliminated and the reaction was stopped.

The mixture was filtered through a bed of diatomaceous earth and the solvent removed under reduced pressure. The residue was dissolved in diethyl ether and the resulting solution washed with ice cold 0.5 N sodium hydroxide solution, until no more turbidity resulted on acidification of the hydroxide wash. The ether solution was then dried (MgSO$_4$) and the solvent then removed under reduced pressure. Trituration of the residue with petroleum ether (30°-60°) afforded 31.7 g of 3α,12α-diacetoxycholan-24-al, mp 152°-155°. A second crop of 5.8 g, mp 145°, was obtained.

Anal. Calcd for $C_{28}H_{44}O_5$: C, 73.00; H, 9.63. Found: C, 73.24; H, 9.77.

EXAMPLE 6

7-(3α,12α-Diacetoxy-5 pregnane-20-yl)-trans,trans-2,4-heptadienoic acid ethyl ester To a solution of 19.6 g of freshly distilled triethyl 4-phosphonocrotonate in 50 ml of dry glyme was added (at −70°) 50 ml of a 1.6 M solution of butyl lithium in hexane. After 15 min the temperature was brought to −10° and 30 g of 3α,12α-diacetoxycholan-24-al was dissolved in 200 ml of dry glyme was added dropwise. After stirring for 20 min at this temperature the reaction mixture was allowed to warm to room temperature and stirred for 0.5 hr. The reaction mixture was then poured into 2 liters of a 5% monobasic sodium phosphate solution and the mixture extracted with ether. The ether solution was washed with a saturated aqueous sodium chloride solution and dried (MgSO$_4$). The solvent was removed under reduced pressure and the residue after being dissolved in a minimum amount of benzene was washed through 300 g of silica gel. The column was eluted with 4 liters of benzene and then 4 liters of 0.5% ethyl acetate-benzene solution, and the solids obtained therefrom were combined to give 20.7 g of crude 7-(3α,12α-diacetoxy-5β-pregnane-20-yl)-trans,trans-2,4-heptadienoic acid ethyl ester. Trituration with petroleum ether afforded 13.1 g of 7-(3α,12α-diacetoxy-5β-pregnane-20-yl)-trans,trans-2,4-heptadienoic acid ethyl ester, mp 129°-131°, plus a second crop of 2.4 g, mp 128°-130°. Crystallization from methanol afforded the analytical sample, mp 130°-132°.

Anal. Calcd for $C_{34}H_{52}O_6$: C, 73.35; H, 9.41. Found: C, 73.13; H, 9.42.

EXAMPLE 7

7-(3α,12α-Dihydroxy-5β-pregnane-20-yl)-trans,trans-3,5-heptadienoic acid

A mixture of 7.25 g of 7-(3α,12α-diacetoxy-5β-pregnane-20-yl)-trans,trans-2,4-heptadienoic acid ethyl ester and 57 ml of 5N aqueous sodium hydroxide solution was stirred and refluxed for 1.5 hr. At the end of this time, 500 ml of water was added and the mixture heated to reflux. The cloudy solution was cooled, charcoal added and the mixture was filtered through a bed of diatomaceous earth. The filtrate was cooled to 0° and made acidic (pH3) by the dropwise addition of concentrated aqueous hydrochloric acid. The precipitate was filtered and air dried overnight under house vacuum. Crystallization from methyl ethyl ketone afforded 4 g of 7-(3α,12α-dihydroxy-5β-pregnane-20-yl)-trans,trans-3,5-heptadienoic acid, mp 208°-211°.

Anal. Calcd for $C_{28}H_{44}O_4$: C, 75.63; H, 9.97. Found: C, 75.71; H, 10.03.

EXAMPLE 8

7-(3α,12α-Dihydroxy-5β-pregnane-20-yl)heptanoic acid

A mixture of 1 g of 10% Pd/C and 7 g of 7-(3α,12α-diacetoxy-5β-pregnane-20-yl)-trans, trans-2,4-heptadienoic acid ethyl ester in 100 ml of ethyl acetate was hydrogenated at atmospheric pressure. After completion of the reaction, the catalyst was filtered and the solvent removed under reduced pressure. The reaction mixture was then treated with 50 ml of 5N aqueous sodium hydroxide solution and refluxed for 2 hr. At the end of this time, 300 ml of water was added followed by a small amount of charcoal. The mixture was filtered through a bed of diatomaceous earth and the filtrate was acidified at 0° by the dropwise addition of conc. aqueous hydrochloric acid. The precipitate was filtered and dried overnight under house vacuum. Crystallization from methyl ethyl ketone afforded 2.5 g of 7(3α,12α-dihydroxy-5β-pregnane-20-yl) heptanoic acid, mp 182°–185°.

Anal. Calcd for $C_{28}H_{48}O_4$: C, 74.95; H, 10.78. Found: C, 74.67; H, 10.78.

EXAMPLE 9

A Tablet (Wet Granulation) was formulated as follows:

| Item | Ingredient | mg/tablet |
|---|---|---|
| 1. | 7-(3α,12α-Dihydroxy-5β-pregnane-20-yl)-trans,trans-3,5-heptadienoic acid | 100 |
| 2. | Lactose | 98.5 |
| 3. | Polyvinyl pyrrolidone | 15 |
| 4. | Modified starch | 15 |
| 5. | Corn starch | 15 |
| 6. | Magnesium stearate | 1.5 |
|  | Weight of tablet | 245 mg |

Procedure:
(1) Mix items 1, 2, 4 and 5 in a suitable mixer, granulate with polyvinyl pyrrolidone and dissolve in water/alcohol. Dry the granulation. Mill the dry granulation through a suitable mill.
(2) Add magnesium stearate and compress on a suitable press.

EXAMPLE 10

A tablet was formulated by the procedure of Example 9 except that the active ingredient was 5-(3α,12α-Dihydroxy-5β-pregnane-20-yl)-trans-2-pentenoic acid.

EXAMPLE 11

A tablet (Wet granulation) was formulated as follows:

| Item | Ingredient | mg/tablet |
|---|---|---|
| 1. | 7-(3α,12αdihydroxy-5β-pregnane-20-yl)-trans,trans-3,5-heptadienoic acid | 250 |
| 2. | Lactose | 100 |
| 3. | Pregelatinized starch | 30 |
| 4. | Modified starch | 50 |
| 5. | Corn starch | 50 |
| 6. | Magnesium stearate | 5 |
|  | Weight of tablet | 500 |

Procedure:
1. Mix items 1, 2, 3, 4 and 5 in a suitable mixer, granulate with water, and dry over night in a suitable oven. Mill through suitable mill.
2. Mix with item 6 and compress on a suitable press.

EXAMPLE 12

A capsule was formulated as follows:

| Item | Ingredient | mg/capsule |
|---|---|---|
| 1. | 7-(3α,12α-dihydroxy-5β-pregnane-20-yl)-trans,trans-3,5-heptadienoic acid | 100 |
| 2. | Lactose | 99 |
| 3. | Corn starch | 20 |
| 4. | Talc | 5 |
| 5. | Magnesium stearate | 1 |
|  | Fill weight of capsule | 225 |

Procedure:
1. Mix items 1, 2 and 3 in a suitable mixer. Mill through a suitable mill.
2. Mix the mixture in Step 1 with item 4 and 5 and fill on a suitable machine.

EXAMPLE 13

| Item | Ingredient | mg/tablet |
|---|---|---|
| 1. | 7-(3α,12α-dihydroxy-5β-pregnane-20-yl) heptanoic acid | 250 |
| 2. | Lactose | 147.5 |
| 3. | Polyvinyl pyrrolidone | 30 |
| 4. | Modified starch | 30 |
| 5. | Corn starch | 30 |
| 6. | Magnesium stearate | 2.5 |
|  | Weight of tablet | 490 mg |

Procedure:
1. Mix items 1, 2, 4 and 5 in a suitable mixer, granulate with PVP and dissolve in water/alcohol. Dry the granulation. Mill the dry granulation through a suitable mill.
2. Add magnesium stearate and compress on a suitable press.

EXAMPLE 14

A tablet (Wet granulation) was formulated as follows:

| Item | Ingredient | mg/tablet |
|---|---|---|
| 1. | 7-(3α,12-dihydroxy-5β-pregnane-20-yl) heptanoic acid | 100 |
| 2. | Lactose | 147.5 |
| 3. | Pregelatinized starch | 25 |
| 4. | Modified starch | 25 |
| 5. | Corn starch | 25 |
| 6. | Magnesium stearate | 2.5 |
|  | Weight of tablet | 325 |

Procedure:
1. Mix items 1, 2, 3, 4 and 5 in a suitable mixer, granulate with water, and dry over night in a suitable oven. Mill through suitable mill.
2. Mix with item 6 and compress on a suitable press.

EXAMPLE 15

A capsule was formulated as follows:

| Item | Ingredient | mg/capsule |
|---|---|---|
| 1. | 7-(3α,12-dihydroxy-5β-pregnane-20-yl) heptanoic acid | 100 |
| 2. | Lactose | 99 |
| 3. | Corn Starch | 20 |

-continued

| Item | Ingredient | mg/capsule |
|---|---|---|
| 4. | Talc | 5 |
| 5. | Magnesium stearate | 1 |
|  | Fill weight of capsule | 225 |

Procedure:
1. Mix items 1, 2 and 3 in a suitable mixer. Mill through a suitable mill.
2. Mix the mixture in Step 1 with item 4 and 5 and fill on a suitable machine.

We claim:
1. A compound of the formula:

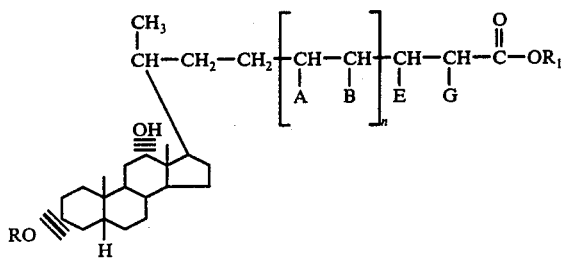

wherein R is hydrogen or lower alkanoyl; $R_1$ is lower alkyl or hydrogen, A and B are individually hydrogen or taken together form a carbon to carbon bond; $n$ is an integer from 0 to 1; E and G are individually hydrogen or taken together form a carbon to carbon bond; with the proviso that when $n$ is 1 and A and B are hydrogen, E and G are also hydrogen and pharmaceutically acceptable salts thereof.

2. The compound of claim 1 where $n$ is 0.
3. The compound of claim 2 wherein said compound is 5-(3α,12α-diformyloxy-5β-pregnane-20-yl)-2-pentanoic acid methyl ester.
4. The compound of claim 2 wherein said compound is 5-(3α,12α-dihydroxy-5β-pregnane-20-yl)-2-pentanoic acid.
5. The compound of claim 2 wherein said compound is 5-(3α,12α-dihydroxy-5β-20-yl)-pentanoic acid.
6. The compound of claim 1 where $n$ is 1.
7. The compound of claim 6 wherein said compound is 7-(3α,12α-diacetoxy-5β-pregnane-20-yl)-2,4-heptadienoic acid ethyl ester.
8. The compound of claim 6 wherein said compound is 7-(3α,12α-dihydroxy-5β-pregnane-20-yl)-3,5-heptadienoic acid.
9. The compound of claim 6 wherein said compound is 7-(3α,12α-dihydroxy-5β-pregnane-20-yl)-heptanoic acid.

* * * * *